United States Patent
Elsheikh et al.

(10) Patent No.: US 6,211,421 B1
(45) Date of Patent: Apr. 3, 2001

(54) PREPARATION OF 1,1,1-TRIFLUOROPROPENE

(75) Inventors: Maher Y. Elsheikh; Bin Chen, both of Tredyffrin, PA (US)

(73) Assignee: Atofina Chemicals, Inc., Philadelphia, PA (US)

( * ) Notice: Subject to any disclaimer, the term of this patent is extended or adjusted under 35 U.S.C. 154(b) by 0 days.

(21) Appl. No.: 09/669,365

(22) Filed: Sep. 26, 2000

(51) Int. Cl.⁷ .................................................... C07C 17/20
(52) U.S. Cl. ............................................................. 570/160
(58) Field of Search ................................................ 570/160

(56) References Cited

U.S. PATENT DOCUMENTS

| 3,739,036 | 6/1973 | Valicenti et al. |
| 4,220,608 | * 9/1980 | Feiring .................................. 570/160 |
| 4,465,786 | * 8/1984 | Zimmer et al. ...................... 570/160 |

* cited by examiner

*Primary Examiner*—Alan Siegel

(57) ABSTRACT

An uncatalyzed liquid phase process is provided for producing 1,1,1-trifluoropropene via the fluorination of 1,1,3-trichloro-1-propene.

1 Claim, No Drawings

PREPARATION OF 1,1,1-TRIFLUOROPROPENE

BACKGROUND OF THE INVENTION

This invention relates to the preparation of 1,1,1-trifluoropropene ("TFP") via the uncatalyzed liquid phase fluorination of 1,1,3-trichloro-1-propene ("TCP") TCP is an intermediate in the manufacture of methyl trifluoropropylsilicone.

The patent literature (U.S. Pat. No. 3,739,036) discloses that the fluorination of TCP is conducted using sodium fluoride as a catalyst.

BRIEF SUMMARY OF THE INVENTION

An uncatalyzed liquid phase process for preparing TFP by the fluorination of TCP is provided, which process comprises (a) contacting said TCP with hydrogen fluoride under conditions sufficient to produce said TFP, and (b) separating the TFP product from the resulting reaction mixture in (a).

DETAILED DESCRIPTION

It has now been discovered that TCP can be fluorinated to produce TFP without the use of catalysts.

The process of this invention can be conducted as a batch or semi-continuous process. The HF:TCP molar ratio is typically from at least about 3:1 to about 300:1, but is preferably from about 5:1 to about 200:1. Temperatures of from about 20° C. to about 200° C. are typically used, preferably from about 30° C. to about 150° C. Residence time is normally from about 1 minute to 4 hours, preferably from about ½ hour to about 3 hours. The pressure is not critical and is dependent on the other process conditions. The product obtained, together with excess HF and HCl, the principal by-product, can be separated by conventional methods such as fractional distillation.

The practice of the invention is illustrated in more detail in the following non-limiting example.

EXAMPLE

Preparation of TFP: 8.25 Moles (165 grams) of HF and 0.055 mole (8 grams) of TCP were heated at 100° C. for 1 hour in an autoclave. When the pressure reached 600 psig, the autoclave was vented. The product was recovered and identified by gas chromatograph/mass spectrometry as TFP (greater than 99% selectivity).

What is claimed is:

1. An uncatalyzed liquid phase process for producing 1,1,1-trifluoropropene which comprises (a) contacting 1,1,3-trichloro-1-propene with hydrogen fluoride under conditions sufficient to produce 1,1,1-trifluoropropene and (b) separating the 1,1,1-trifluoropropene product from the resulting reaction mixture in (a).

* * * * *